US008374309B2

(12) United States Patent
Donath et al.

(10) Patent No.: US 8,374,309 B2
(45) Date of Patent: Feb. 12, 2013

(54) ARRANGEMENT AND METHOD FOR PROJECTIVE AND/OR TOMOGRAPHIC PHASE-CONTRAST IMAGING USING X-RAY RADIATION

(75) Inventors: Tilman Donath, Brugg (CH); Martin Hoheisel, Erlangen (DE); Christian David, Lauchringen (DE); Eckhard Hempel, Fürth (DE); Franz Pfeiffer, Garching (DE); Stefan Popescu, Erlangen (DE)

(73) Assignees: Siemens Aktiengesellschaft, Munich (DE); Paul Scherrer Institut, Villigen, PSI (CH)

( * ) Notice: Subject to any disclaimer, the term of this patent is extended or adjusted under 35 U.S.C. 154(b) by 323 days.

(21) Appl. No.: 12/686,404

(22) Filed: Jan. 13, 2010

(65) Prior Publication Data
US 2010/0177864 A1   Jul. 15, 2010

(30) Foreign Application Priority Data

Jan. 15, 2009   (DE) .................. 10 2009 004 702

(51) Int. Cl.
H05G 1/64 (2006.01)
A61B 6/03 (2006.01)
G01N 23/083 (2006.01)
G21K 1/00 (2006.01)
G21K 3/00 (2006.01)

(52) U.S. Cl. ............... 378/19; 378/36; 378/62; 378/145; 378/157; 378/158

(58) Field of Classification Search .................... 378/19, 378/62, 70, 71, 86, 87, 36, 145, 156–158
See application file for complete search history.

(56) References Cited

U.S. PATENT DOCUMENTS

| | | | | |
|---|---|---|---|---|
| 7,433,444 B2 * | 10/2008 | Baumann et al. | ............... | 378/62 |
| 7,453,981 B2 * | 11/2008 | Baumann et al. | ............... | 378/62 |
| 7,486,770 B2 * | 2/2009 | Baumann et al. | ............... | 378/62 |
| 7,492,871 B2 * | 2/2009 | Popescu et al. | ................ | 378/145 |
| 7,522,698 B2 * | 4/2009 | Popescu et al. | ................ | 378/19 |

(Continued)

FOREIGN PATENT DOCUMENTS

| | | |
|---|---|---|
| DE | 102006015356 A1 | 8/2007 |
| DE | 102006015358 A1 | 8/2007 |

(Continued)

OTHER PUBLICATIONS

C. Kottler et al., "A two-directional approach for grating based differential phase contrast imaging using hard x-rays", Optics Express vol. 15, No. 3, Feb. 5, 2007, pp. 1175-1181.

(Continued)

*Primary Examiner* — Allen C. Ho
(74) *Attorney, Agent, or Firm* — Harness, Dickey & Pierce, P.L.C.

(57) ABSTRACT

An arrangement and a method are disclosed for projective and/or tomographic phase-contrast imaging using X-ray radiation. In at least one embodiment, one or more phase grids is/are arranged in the beam path such that during a rotation of the at least one X-ray source, the examination object is scanned with different spatial orientations of the grid lines relative to the examination object such that the complete refraction angle, and hence the complete phase shift gradient, can be determined for each X-ray beam from the two scans with differently oriented phase grids in order to be able to show the phase shift of an examination object in terms of projections or in a tomographic image.

27 Claims, 9 Drawing Sheets

U.S. PATENT DOCUMENTS

| | | | |
|---|---|---|---|
| 7,522,708 B2 * | 4/2009 | Heismann et al. | 378/145 |
| 7,532,704 B2 * | 5/2009 | Hempel | 378/19 |
| 7,535,986 B2 * | 5/2009 | Hempel | 378/4 |
| 7,561,658 B2 * | 7/2009 | Hempel et al. | 378/4 |
| 7,564,941 B2 * | 7/2009 | Baumann et al. | 378/19 |
| 7,639,786 B2 * | 12/2009 | Baumann et al. | 378/145 |
| 7,646,843 B2 * | 1/2010 | Popescu et al. | 378/5 |
| 7,817,777 B2 * | 10/2010 | Baumann et al. | 378/62 |
| 7,889,838 B2 * | 2/2011 | David et al. | 378/36 |
| 7,920,673 B2 * | 4/2011 | Lanza et al. | 378/62 |
| 7,945,018 B2 * | 5/2011 | Heismann et al. | 378/62 |
| 7,949,095 B2 * | 5/2011 | Ning et al. | 378/62 |
| 7,983,381 B2 * | 7/2011 | David et al. | 378/4 |
| 8,005,185 B2 * | 8/2011 | Popescu | 378/36 |
| 8,009,796 B2 * | 8/2011 | Popescu et al. | 378/19 |
| 2007/0183560 A1 | 8/2007 | Popescu et al. | |
| 2007/0183563 A1 | 8/2007 | Baumann et al. | |
| 2007/0183580 A1 | 8/2007 | Popescu et al. | |
| 2009/0092227 A1 | 4/2009 | David et al. | |

FOREIGN PATENT DOCUMENTS

| | | |
|---|---|---|
| DE | 102006017291 A1 | 8/2007 |
| DE | 102006037255 A1 | 8/2007 |
| WO | WO 2006131235 A1 | 12/2006 |

OTHER PUBLICATIONS

Anton Maksimenko et al., "Computed tomographic reconstruction based on x-ray refraction contrast", Applied Physics Letters 86, 124105 (2005).

F. Pfeiffer et al., "Hard X-Ray Phase Tomography with Low-Brilliance Sources", Physical Review Letters, 108105, Mar. 9, 2007, vol. 98, No. 10.

Jiang M. et al., "X-Ray Phase-Contrast Imaging with Three 2D Gratings", Int. Journal of Biomedical Imaging, vol. 2008, pp. 1-8.

German Office Action dated Dec. 11, 2009.

Avinash C.Kak, Malcolm Slaney; Principles of Computerized Tomographic Imaging Kapitel 3.5; IEEE Press, New York, 1988, pp. 96-99; Book; 1998.

Weitkamp, Timm et al.; X-ray phase imaging with a grating interferometer; Optics Express, vol. 13, No. 16, published Aug. 8, 2005, pp. 6296-6304; Optical Society of America; 13; Magazine; 2005.

Chapman, D. et al.; Diffraction enhanced x-ray Imaging; Phys. Med. Biol., vol. 42, 1997, pp. 2015-2025; IOP Publishing Ltd.; 42; 0031-9155/97; Magazine; 1997.

Pfeiffer, Weitkamp et al.; Phase retrieval and differential phase-contrast imaging with low-brilliance X-ray sources; Nature Physics, vol. 2, pp. 258-261; 2006.

Anton Maksimenko et al., "Computed tomographic reconstruction based on x-ray refraction contrast", Applied Physics Letters 86, 124105 (2005), pp.

T. Holland & H. Holland, "A mathematical model of immunohistochemical preparations, which provides quantitative predictions", Journal of Microscopy, vol. 214, Apr. 2004, pp. 7-12.

F. Pfeiffer et al., "Hard X-Ray Phase Tomography with Low-Brilliance Sources", Physical Review Letters, 108105, März 9, 2007, vol. 98, No. 10.

Gregory W. Faris et al. "Beam-deflection optical tomography", Optics Letters, vol. 12, No. 2, Feb. 1987, pp. 72-74.

Frederic Noo et al. "A two-step Hilbert transform method for 2D image reconstruction", Phys. Med. Biol. 49 (2004), pp. 3903-3923.

Zhi-Feng Huang et al., "Direct computed tomographic reconstruction for directional-derivative projections of computed tomography of diffraction enhanced imaging", Applied Physics Letters 89,(2006), pp. 041124-1-041124-3.

F. Pfeiffer et al., "Tomographic reconstruction of three-dimensional objects from hard X-ray differential phase contrast projection images", Nuclear Instruments and Methods in Physics Researh A 580 (2007), pp. 925-928.

F.A. Dilmanian et al., "Computed tomography of x-ray index of refraction using the diffraction enhanced imaging method", Phys. Med. Biol. 45 (2000), pp. 933-946.

* cited by examiner

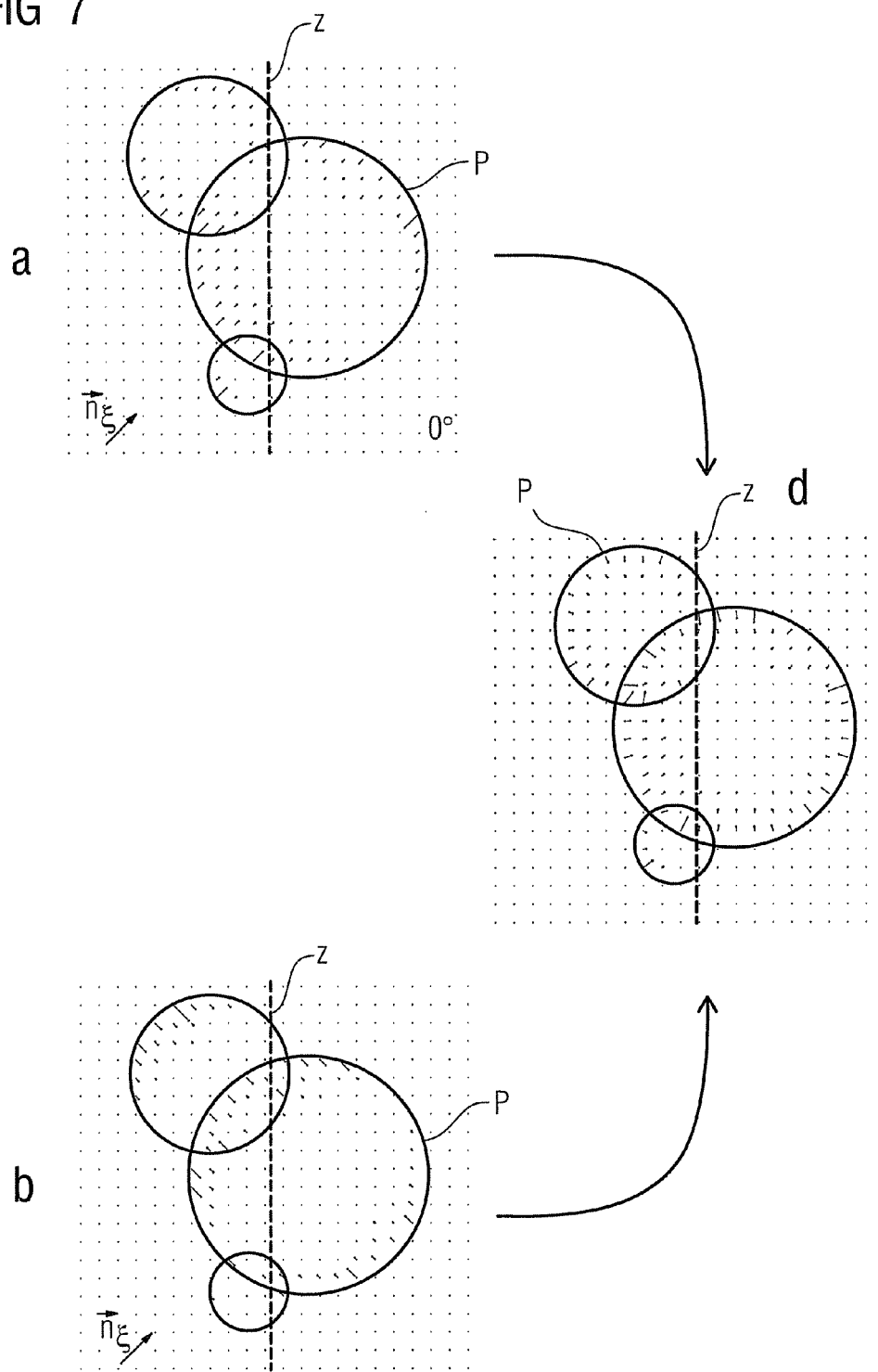

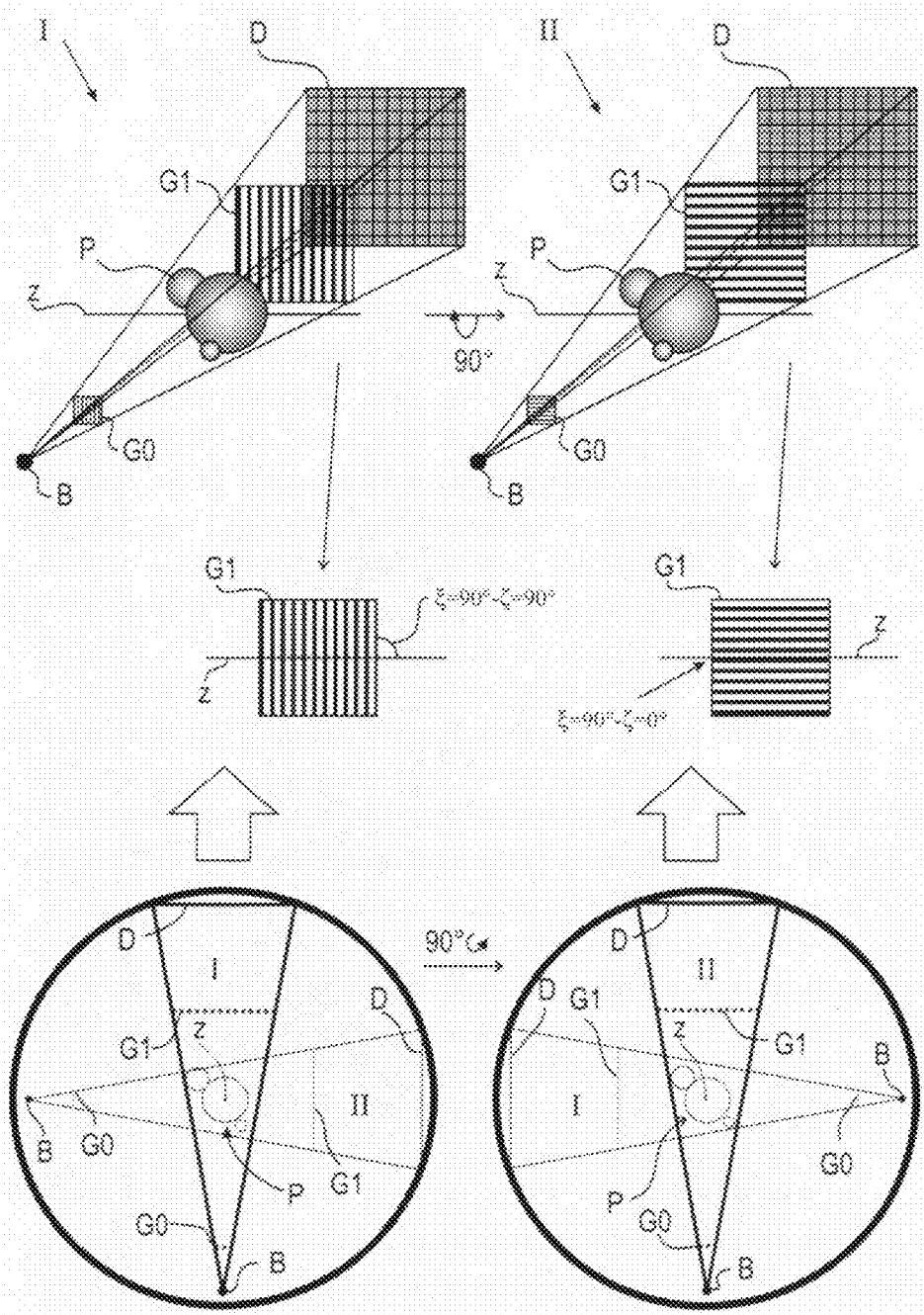

detector element detector stripes detector stripes detector element

ARRANGEMENT AND METHOD FOR PROJECTIVE AND/OR TOMOGRAPHIC PHASE-CONTRAST IMAGING USING X-RAY RADIATION

PRIORITY STATEMENT

The present application hereby claims priority under 35 U.S.C. §119 on German patent application number DE 10 2009 004 702.6 filed Jan. 15, 2009, the entire contents of which are hereby incorporated herein by reference.

FIELD

At least one embodiment of the invention generally relates to an arrangement for projective and/or tomographic phase-contrast imaging using X-ray radiation. In at least one embodiment it more specifically relates to an arrangement with at least one coherent or quasi-coherent X-ray source which generates a beam path, and a measurement field in which an examination object can be positioned, wherein a phase grid with grid lines for generating an interference pattern is positioned in the beam path and a readout arrangement for the generated interference pattern is arranged downstream of the phase grid and detects the change in the frequency pattern during a phase scan, wherein the at least one X-ray source with the associated phase grid and the readout arrangement is designed such that, relative to the examination object, it can rotate about a system axis. Moreover, at least one embodiment of the invention also generally relates to a method for generating projective and/or tomographic image data records with differential phase contrast using X-ray radiation, in particular by using the above-described arrangement.

BACKGROUND

An arrangement and a method in differential phase-contrast computed tomography (DPC-CT) using X-ray radiation is able to not only illustrate the three-dimensional or layered distribution of the attenuation coefficient $\mu(x,y,z)$, but can also reconstruct the refractive index $n=1-\delta(x,y,z)$ from the measured data. In order to achieve this, the angle of refraction, that is to say a small deflection of the X-ray radiation when passing through an object, is also measured in a spatially resolved fashion in the projections in addition to the intensity of the transmitted X-ray radiation. In order to measure this angle of refraction, use is made of the design of a Talbot interferometer, possibly with the additional use of a source grid. In respect of such an arrangement and such a method, reference is made in an exemplary fashion to the documents DE 10 2006 037 255 A1, DE 10 2006 017 291 A1 and DE 10 2006 015 356 A1.

However, these known arrangements and methods only measure one component of the angle of refraction, that is to say the angle in the plane spanned by the beam direction and the normal of the grid structure, using the one-dimensional phase grids described therein. Accordingly, phase information at an angle to the plane spanned by the beam direction and the normal of the grid structure is only reproduced in a reduced fashion or not at all.

SUMMARY

In at least one embodiment of the invention, an arrangement and a method are disclosed for projective and/or tomographic phase-contrast imaging using X-ray radiation which, by using simple one-dimensional phase grids, afford the possibility of determining the complete angle of refraction, and hence the complete phase shift gradient, within the scope of a scan in order to be able to show the phase shift of an examination object in a projective fashion or in a tomographic illustration.

This document describes how, in a simple fashion, it is possible for the complete angle of refraction or two linearly independent directional derivatives of the phase projection to be measured using a one-dimensional Talbot interferometer. A method by which the complete gradient information measured in this fashion can be converted into two directional derivatives which are directly suitable for the tomographic reconstruction using existing reconstruction methods is also illustrated.

To this end, the inventors have recognized the following:

A grid interferometer, also known as a Talbot interferometer, with one-dimensional grid structures as described in, for example, the abovementioned documents or in "Interferometer for quantitative phase contrast imaging and tomography with an incoherent polychromatic X-ray source" by C. David, F. Pfeiffer and T. Weitkamp, is used for the projection measurement, the entire contents of which are hereby incorporated herein by reference. When using minimally fanned beams, these grids are usually planar and are oriented perpendicularly with respect to the incident beam. If divergent beams are used, the grids can also be spherical and/or be arranged around the source point.

For measurement purposes, a so-called phase scan is performed for each projection using the interferometer. This determines for each detector pixel the average intensity and the direction of the radiation downstream of the examination object. As a result of normalizing the signals with respect to a reference projection without an examination object, the projection of the linear attenuation coefficient is obtained as in conventional CT and, additionally, an image of the angles of refraction or gradient vectors. However, the measured angles of refraction only contain the component of the angle of refraction that is situated in the plane spanned by the beam direction and the normal of the grid structure. To a good approximation, the angle of refraction is given by $\vec{\nabla}p$, the gradient of the projection $p=\int \delta(x,y,z)ds$ of the refractive index along the projection direction (=beam direction). Thus, the Talbot interferometer in each case measures a directional derivative of p and not the complete gradient $\vec{\nabla}p$.

For the purposes of a simpler illustration, the assumption can first of all be made that the beams are arranged in parallel and that the grids are planar and lie in a tz-plane, as illustrated in FIG. 1. The orientation of the grid structures is described by the angle $\xi$ between the t-axis and the normal of the grid lines. The normal of the grid structure $$\vec{n}_\xi = \begin{bmatrix} \cos\xi \\ \sin\xi \end{bmatrix}$$

in the tz-coordinate system then precisely describes the direction of the directional derivative of p measured by the interferometer. The vector $\vec{n}_\xi$ is perpendicular to the grid lines and points in the direction for which the phase gradient is determined. For the complete gradient, $$\vec{\nabla}p = \begin{bmatrix} \frac{\partial p}{\partial t} \\ \frac{\partial p}{\partial z} \end{bmatrix},$$

the directional derivative along the direction $\vec{n}_\xi$ is given by $$\frac{\partial p}{\partial n_\xi} = \vec{n}_\xi \cdot \vec{\nabla} p,$$

the scalar product of the vectors $\vec{n}_\xi$ and $\vec{\nabla}p$.

Projections of many different projection angles can be recorded for the tomographic reconstruction of $\delta(x,y,z)$ as is described in, for example, Weitkamp et al., Optics Express 12, 6296, 2005 and Pfeiffer et al., Phys Rev Lett 98, 108105, 2007, the entire contents of each which are hereby incorporated herein by reference. Advantageously, on the laboratory scale, the examination object can in this case be rotated about a rotational axis perpendicular to the X-ray beam or, in a large-scale application, the X-ray source with the phase grid and readout arrangement is rotated about the examination object. For simplicity, the examination object is now, in accordance with the illustration in FIG. 1, defined to be rotated about the z-axis for projection measurements. In the process, the relative rotation of the examination object is described by the projection angle θ. Accordingly, the projections, which are only expressed as p, should be understood to be functions p(t,z,θ).

The angle $\xi$ and the normal of the grid structure $\vec{n}_\xi$ describe the relative orientation of the measured directional derivative with respect to the tomographic rotational axis. In the special cases $\xi=0°$ and $\xi=90°$, the directional derivatives, $$\frac{\partial p}{\partial n_{\xi=0°}} = \frac{\partial p}{\partial t}$$

and $$\frac{\partial p}{\partial n_{\xi=90°}} = \frac{\partial p}{\partial z},$$

that is to say precisely the directional derivatives along the t- and the z-axis, i.e. perpendicular to or parallel to the rotational axis, are measured. As will be explained further down, these directional derivatives are of particular importance to the tomographic reconstruction. However, any other angles $\xi$ can be selected for the measurement.

If the projection p can be reconstructed from the measured directional derivatives $\partial p/\partial n_\xi$, then conventional tomographic methods can be used for reconstructing $\delta(x,y,z)$. For example, p can be calculated by numerically integrating a single directional derivative for an angle $\xi$ if a constant of integration is known e.g. the value of p at the edge of the projection. The projection obtained in this fashion can be reconstructed using conventional tomographic reconstruction algorithms. A plurality of directional derivatives at different angles $\xi_i$, i=1, 2, . . . , can be integrated numerically in this fashion. Subsequently, the projections $p_i$ obtained for all $\xi_i$ can be superposed in a weighted fashion.

Other methods afford the possibility of determining the projection p(t,z) directly from a plurality of directional derivatives. In this respect, reference is made to the document C. Kottler et al., Optics Express 15, 3, 1175-1181, 2007, the entire contents of which are hereby incorporated herein by reference, which describes a method whereby two measured orthogonal directional derivatives, e.g. $\partial p/\partial n_{\xi=0°}$ and $\partial p/\partial n_{\xi=90°}$ measured at $\xi=0°$ and $\xi=90°$, are combined. To this end, $$p(t, z) = IFT\left[2\pi i(k + il)FT\left(\frac{\partial p(t, z)}{\partial n_{\xi=0°}} + i\frac{\partial p(t, z)}{\partial n_{\xi=90°}}\right)\right]$$

is calculated, wherein FT is the two-dimensional Fourier transform from the position space t, z into the frequency space k, l, and IFT is the corresponding inverse Fourier transform.

Since the reconstruction of p from a plurality of linearly independent directional derivatives generally constitutes an over-defined problem, optimization strategies can also be applied for the reconstruction of p.

However, it is not mandatory to determine the projection p before the tomographic reconstruction. The following text describes how tomographic displays of the phase shift can also be reconstructed using the directional derivatives, that is to say the gradient vectors of the phase shift.

In respect of the tomographic reconstruction of the directional derivatives, a distinction has to be made between the cases $\xi=0°$ and $\xi=90°$.

"In-plane" gradient reconstruction (case $\xi=0°$): When $\xi=0°$, the rotational axis is oriented parallel to the grid structures and the directional derivative $\partial p/\partial t$ perpendicular to the rotational axis, or in the reconstruction plane, is measured. The distribution $\delta(x,y,z)$ can be reconstructed directly from the directional derivatives if an adapted reconstruction method is used which takes into account the particular differential property of the data. In this respect, reference is made to the documents G. W. Faris and R. L. Byer, Optics Lett. 12, No. 2, pp. 72-74, 1987; Noo et al., Phys. Med. Biol. 49, pp. 3903-3923, 2004; Huang et al., J. Phys. D, 39, 2925; and F. Pfeiffer et al., Nucl. Instrum. Methods Phys. Res. A, 580, 925-928, 2007, the entire contents of each of which are hereby incorporated herein by reference. A similar reconstruction method calculates directional derivatives in the layers from the directional derivatives in the projection [A. Maksimenko, Appl. Phys. Lett. 86, 124105, 2005, the entire contents of which are hereby incorporated herein by reference].

"Out-of-plane" gradient reconstruction (case $\xi=90°$): When $\xi=90°$, the rotational axis is oriented perpendicular to the grid structures and the directional derivative $\partial p/\partial z$ in the z-direction, that is to say perpendicular to the reconstruction plane, is measured. The z-gradient $$\frac{\partial}{\partial z}\delta(x, y, z)$$

in the object is independent of the rotation of the examination object, that is to say from the projection angle θ. Thus, $$\frac{\partial}{\partial z}\delta(x, y, z)$$

can be reconstructed in a tomographic fashion from the measured directional derivatives (=projections) using conventional reconstruction methods. In respect of such reconstruction methods, reference is made in an exemplary fashion to the document Dilmanian et al., 2000, Phys. Med. Biol. 45, 4, pp. 933-946, the entire contents of which are hereby incorporated herein by reference. Numerical integration along the z-axis also affords the possibility of reconstructing $\delta(x,y,z)$ from the reconstructed $$\frac{\partial}{\partial z}\delta(x, y, z)$$

if a constant of integration is known for each x, y. For example, typically $\delta(x,y,z)=0$ is known at the edge or outside of the examination object.

Although, the object can, in principle, be reconstructed in a tomographic fashion from only one measured directional derivative, the invention provides for an improvement in the reconstruction by measuring the complete gradient vector and using the latter in the reconstruction. In order to measure the two directional derivatives $\partial p/\partial t$ and $\partial p/\partial z$, two measurements have to be performed for different relative orientations of the grid structures and the examination object. In computed tomography, the measurement of directional derivatives for $\xi=0°$ and $\xi=90°$ requires a rotation of the grid arrangement relative to the rotational axis.

In accordance with the method illustrated here, it is proposed to perform respectively two measurements with different orientations of the phase grid, and therefore also of the readout arrangement and, possibly, of the source grid as well. Such a reorientation of the grids requires much time and effort and is hardly possible when applied to, in particular, a living organism because too much time passes between measurements for it to be possible for the examination object to be scanned in an identical position. Thus, it would be advantageous to perform both measurements simultaneously in a CT examination. By way of example, this can be effected using a so-called dual source CT, in which every emitter-detector system is used with grids of differing orientation. If the emitter-detector systems are in this case arranged on a common gantry and offset with respect to each other by an angle of 90°, scanning using both grid orientations is possible almost simultaneously without the risk of too much spatial unsharpness as a result of motion of the examination object. However, a disadvantage of such an arrangement is the relatively high expenditure as a result of the doubly-present emitter-detector systems.

However, the inventors have also recognized that phase scans using a single emitter-detector system which can pivot or rotate about a system axis are possible if the X-ray optical grids (source grid, phase grid, analysis grid) attached thereon are arranged at an angle $\xi$ (which does not equal $\xi=0°$ or $\xi=90°$) relative to the system axis—to be more precise, relative to the projection of the system axis in the beam path onto the grids. To this end, on a laboratory scale, the rotational axis present for setting the projection angle can be used in DPC-CT. The object or the examination object is rotated about this axis, with the orientation being described by the angle $\theta$. In the CT system scale for examining a patient, the X-ray optical grids have to be installed with an appropriate orientation in respect of the system axis. In the case of such an "oblique" orientation of the grids, the phase scan is respectively performed with grids having differing orientations relative to the examination object after a relative rotation of the object of 180° with respect to the emitter-detector system, that is to say in the case of a scan along the same projection axis but in the opposite direction.

By evaluating such projection pairs, recorded at projection angles of $\theta_1$ and $\theta_2=\theta_1+180°$, the gradient is thus in each case determined perpendicularly with respect to the grid lines. By tilting the grid relative to the rotational axis about the angle $\xi$, the projections measured at $\theta_1$ and $\theta_2$, that is to say at an offset of 180°, then correspond to the gradient along different spatial directions in the system of the examination object. Thus, in general, the two projections are no longer mirror images of each other and the measured gradient of the second measurement is not parallel to the gradient of the first measurement. Of course, this only holds for $\xi \neq n*90°$, with n=0, 1, 2, 3, . . . . In the special case $\xi=45°$, the two measured gradients are precisely orthogonal with respect to one another.

Therefore, the gradient for any direction can be calculated by combining both measurements. Mathematically, this can be expressed as follows: the directional derivatives $$\frac{\partial p_{\theta=0°}}{\partial n_\xi} = \vec{n}_\xi \cdot \vec{\nabla} p_{\theta=0°} = \begin{bmatrix} \cos\xi \\ \sin\xi \end{bmatrix} \cdot \begin{bmatrix} \frac{\partial p_{\theta=0°}}{\partial t} \\ \frac{\partial p_{\theta=0°}}{\partial t} \end{bmatrix} \qquad \text{Eq. (1)}$$

and $$\frac{\partial p_{\theta=180°}}{\partial n_\xi} = \vec{n}_\xi \cdot \vec{\nabla} p_{\theta=180°} = \begin{bmatrix} \cos\xi \\ \sin\xi \end{bmatrix} \cdot \begin{bmatrix} -\frac{\partial p_{\theta=0°}}{\partial t} \\ \frac{\partial p_{\theta=0°}}{\partial t} \end{bmatrix} \equiv \vec{n}'_\xi \cdot \vec{\nabla} p_{\theta=0°} \qquad \text{Eq. (2)}$$

are measured for two projections. For simplicity, projection angles of $\theta=0°$ and 180° have been assumed in this case. Use has been made of the fact that $$\frac{\partial p_{\theta=180°}}{\partial t} = -\frac{\partial p_{\theta=0°}}{\partial t}.$$

Equation (2) shows that the directional derivative of the projection at $\theta=180°$ precisely corresponds to the directional derivative in the direction of $$\vec{n}'_\xi = \begin{bmatrix} -\cos\xi \\ \sin\xi \end{bmatrix} = \vec{n}_{180°-\xi}.$$

The vector $\vec{n}'_\xi$ introduced in the previous equation corresponds to the mirror image of $\vec{n}_\xi$ in the z-axis. The measurement principle is illustrated in FIGS. 4 and 7 for a simulation of spherical objects.

In order to calculate the gradient directions important for the tomographic reconstruction along the system axis or rotational axis in the z-direction and perpendicular to the rotational axis in the t-direction, the following results from equations (1) and (2) for a prescribed tilting about the angle $\xi$:

$$\frac{\partial p_{\theta=0°}}{\partial t} = \frac{\frac{\partial p_{\theta=0°}}{\partial n_\xi} + \frac{\partial p_{\theta=180°}}{\partial n_\xi}}{2\sin\xi} \quad \text{Eq. (3)}$$

and $$\frac{\partial p_{\theta=0°}}{\partial z} = \frac{\frac{\partial p_{\theta=0°}}{\partial n_\xi} - \frac{\partial p_{\theta=180°}}{\partial n_\xi}}{2\cos\xi}. \quad \text{Eq. (4)}$$

Hence, these fundamental directional derivatives can be determined from the measured directional derivatives for two projections offset by 180°, provided the denominators in equations (3) and (4) do not equal zero. Arbitrary other directional derivatives can also be determined from the measured directional derivatives in a corresponding fashion.

This measurement with "obliquely" oriented grids allows the measurement of the phase gradients of the projection in two mutually independent directions in a simple fashion, without in the process having to change the grid arrangement, to be more precise the grid orientation in the emitter-detector system. Nor does the detector or the examination object have to be rotated about the beam axis. In order to achieve this, a suitable grid orientation with an angle $\xi$ is selected and the examination object is in each case irradiated from two projection directions offset by 180°. The gradients of arbitrary other directions in the projection can in turn be determined from the measured gradients. The rotation of the arrangement or the examination object about the beam axis for measuring a second gradient direction becomes superfluous. The already available CT rotational axis is used to change the orientation of the examination object relative to the grid structure.

The described arrangement results in a decisive advantage for a laboratory arrangement. Since the examination object does not have to be rotated about the beam axis but only about the z-axis for measuring two directional derivatives, the examination object can hang in a liquid tank without difficulties if the z-axis is aligned with the gravitational force.

In principle, the refractive index of the entire layer can already be determined unambiguously from the differential data record ∂p/∂t which is determined perpendicularly to the z-axis. The additional information obtained by the gradient in the z-direction can be used to check consistency in the data or minimize errors in the reconstruction. Both are possible for the projections and the reconstructions. By way of example, the method by Kottler et al. cited above can be used to combine p from two measured orthogonal directional derivatives.

Moreover, the arrangement affords the possibility of measuring the gradient along the perpendicular and parallel directions with differing degrees of accuracy in order to optimally match it to the respective measurement or the respective object. In the extreme cases $\xi=0°$ and $\xi=90°$, only one component of the gradient is measured in each case, the second component is undetermined. The relative accuracy of the gradient measurement for the t and z-directions can be set by a suitable choice of the angle $\xi$.

The method described herein can also be applied in combination with a finitely large incoherent source if an additional source grid G0 designed as an absorption grid is arranged in the beam path downstream of the source in a known fashion. Such an arrangement is described, for example, in F. Pfeiffer et al., Nature Physics 2, pp. 258-261, 2006, the entire contents of which are hereby incorporated herein by reference. It goes without saying that all grid structures are in each case tilted by the same angle $\xi$.

In accordance with the above-described basic idea of the invention, the inventors propose the embodiments of an arrangement and a method for projective and/or tomographic phase-contrast imaging using X-ray radiation described below.

In a known fashion, this arrangement comprises:
at least one coherent or quasi-coherent X-ray source which generates a beam path, and
a measurement field in which an examination object can be positioned, wherein
a one-dimensional phase grid with grid lines for generating an interference pattern is positioned in the beam path,
a readout arrangement for the generated interference pattern is arranged downstream of the phase grid and detects the change in the frequency pattern during a phase scan,
wherein the at least one X-ray source with the associated phase grid and the readout arrangement is designed such that, relative to the examination object, it can rotate about a system axis.

The refinement according to at least one embodiment of the invention of this arrangement comprises the phase grid or grids being arranged in the beam path such that during a rotation of the at least one X-ray source, the examination object is scanned with different spatial orientations of the grid lines relative to the examination object.

In accordance with one embodiment variant of the arrangement, it is proposed that two X-ray sources are provided on a gantry and the phase grids of each X-ray source have a different angle of incidence ($\zeta_1=90°-\xi_1, \zeta_2=90°-\xi_2$) between its grid lines and the system axis projected thereon in the beam direction. Herein, the two angles of incidence ($\zeta_1=90°-\xi_1$, $\zeta_2=90°-\xi_2$) can be perpendicular with respect to each other, preferably they are 0° and 90°. Alternatively, the two angles of incidence ($\zeta_1=90°-\xi_1$, $\zeta_2=90°-\xi_2$) can also be aligned such that the error in the reconstruction is minimized.

In accordance with another embodiment variant of the arrangement, it is proposed that a phase grid is arranged in a beam path from an X-ray source and it has an angle of incidence ($\zeta=90°-\xi$) between its grid lines and the system axis projected thereon in the beam direction which does not equal an integer multiple of a right angle.

Advantageously, the angle of incidence ($\zeta=90°-\xi$) should be set to values between 10° and 80°, preferably between 30° and 60°, preferably 45°, with it being particularly expedient for the angle of incidence ($\zeta=90°-\xi$) to be selected such that the error in the reconstruction is minimized.

It is furthermore proposed in a refinement of the arrangement that the readout arrangement comprises an analysis grid and an at least single-row detector. Alternatively, the readout arrangement can however comprise a detector which has a multiplicity of strip-shaped detection strips which can be read out individually aligned with the grid lines of the phase grid for each detector element. As a result of this, relative motion between the grids can be dispensed with during the phase scan and the position of the intensity maximum on the detector element can be determined directly.

In order to satisfy the coherence requirement needed for the phase-contrast measurement, it is possible, on the one hand, for an almost punctiform X-ray source to be used; however, alternatively, it is also possible for a source grid for generating quasi-coherent radiation to be arranged in the beam path between a relatively large X-ray source and the phase grid. In an analogous fashion, the X-ray source itself can have a strip-shaped design, by e.g. arranging different materials on the anode in strip-shaped fashion or by scanning the anode in a strip-shaped fashion by a directed electron beam.

In addition to the arrangement according to at least one embodiment of the invention, a method for generating projective and/or tomographic image data records with differential phase contrast using X-ray radiation is also proposed, with it being possible for this method to use in particular the above-described embodiment variants of the arrangement. In the process, the proposed method has the following method steps:

scanning on at least one projection axis an examination object with at least one coherent or quasi-coherent X-ray source and at least one one-dimensional phase grid arranged in the beam path, wherein at least two phase scans with a respectively differently oriented phase grid are performed for each projection axis and gradient vectors of the phase shift values are determined in each case, which phase shift values are aligned perpendicularly with respect to the longitudinal direction of the grid lines of the utilized phase grid and situated in the plane of the utilized phase grid, and the complete gradient vectors of the phase shift values with magnitude and direction in the plane of the utilized phase grid are calculated from at least two phase scans of a projection axis.

Within the scope of at least one embodiment of the invention, the projection axis means a spatial axis on which projections with corresponding phase scans can be performed in two opposing directions.

The projection values obtained as a result of this, which reproduce the complete gradient vector of the phase shift values of each X-ray beam when passing through the examination object, can then either be output directly as a projective illustration, or the phase shift values of each X-ray beam as they pass through the examination object can be determined and displayed by integrating the gradient vectors. By way of example, a certain known value of the phase shift can be assumed at the measurement edge or at a defined position in the measurement field and it can be used in the integration as a constant factor.

Once the local phase shift values have been determined for a multiplicity of projection angles over at least 180°, computed tomography image data can be reconstructed from this projection data in a known fashion.

However, instead of a complete calculation of the phase shift values and a reconstruction of tomographic displays from the projective phase shift values obtained previously by integration, it can also be advantageous to dispense with the intermediate step of integration and instead perform the reconstruction directly using the differential measurement values. Advantageously, the reconstruction can also be performed directly using the differential values of the projection.

Accordingly, the inventors also propose a method for generating projective and/or tomographic image data records with differential phase contrast using X-ray radiation, preferably using the above-described arrangement according to at least one embodiment of the invention, comprising the following method steps:

scanning on at least one projection axis an examination object with at least one coherent or quasi-coherent X-ray source and at least one one-dimensional phase grid arranged in the beam path, wherein at least two phase scans with a respectively differently oriented phase grid are performed for each projection axis and gradient vectors of the phase shift values are determined in each case, which phase shift values are aligned perpendicularly with respect to the longitudinal direction of the grid lines of the utilized phase grid and situated in the plane of the utilized phase grid, and tomographic local phase shift values are reconstructed directly from the gradient vectors.

Advantageously, the reconstruction can in this case be performed directly using the two gradient vectors measured perpendicularly with respect to the grid lines of the phase grid.

Moreover, the complete gradient vectors with magnitude and direction can be calculated before the reconstruction from two gradient vectors measured perpendicularly with respect to the grid lines of the phase grid and the reconstruction can be performed therewith.

In order to perform these two above-described method types, there can be for each projection axis two phase scans in opposing directions using the same system comprising X-ray source, phase grid and readout arrangement, with this system respectively being rotated by 180° about a system axis between two phase scans directed in opposing directions. If this method occurs within the scope of a CT measurement, in which a multiplicity of projection directions are scanned, corresponding opposing measurements on the same projection axis are taken into account during the evaluation.

Alternatively, use can be made of at least two projection systems having an X-ray source, a phase grid and a readout arrangement, which systems are arranged at an angular offset on a gantry, wherein the orientation of the phase grids in respect of the projection of the system axis of the gantry in the beam path onto the phase grid differs. Herein, it is expedient if the grid lines of the phase grid of two projection systems form angles of incidence with the system axis projected thereon in the beam path which differ by 90°, preferably forming an angle of incidence, of 0° or 90°.

BRIEF DESCRIPTION OF THE DRAWINGS

In the following text, the invention will be explained in more detail with the aid of the figures on the basis of the preferred example embodiments, with only features required for understanding the invention being illustrated. The following reference signs and variables are utilized: 1: CT system; 2, 4: X-ray tube; 3, 5: detector; 6: gantry housing; 8: couch table; 10: control and computational unit; B: focal spot; D: detector; G0: source grid; G1: phase grid; G2: analysis grid; P: examination object/patient; p: projection; $Prg_1$ to $Prg_n$: computer programs; S: system axis; t: axis in the detector plane perpendicular to the system axis; z: system axis/rotational axis; I: first emitter-detector arrangement; II: second emitter-detector arrangement; γ: X-ray radiation; θ: projection angle; ζ: angle of incidence between the normal of the grid lines and the rotational axis projected in the beam path; ξ: angle between the normal of the grid and the t-axis; $\vec{n}'_g$: normal vector of the grid structure. In detail:

FIG. 7 shows an illustration of the measurement results in the case of three ideal spherical examination objects when using two emitter-detector systems with phase grids respectively tilted by 45° and tilted by 90° with respect to one another;

FIGS. 8a-8c show illustrations of the measurement principle with three ideal spherical examination objects when using two emitter-detector systems with phase grids tilted by 0° and 90°, respectively.

DETAILED DESCRIPTION OF THE EXAMPLE EMBODIMENTS

Figure 1:
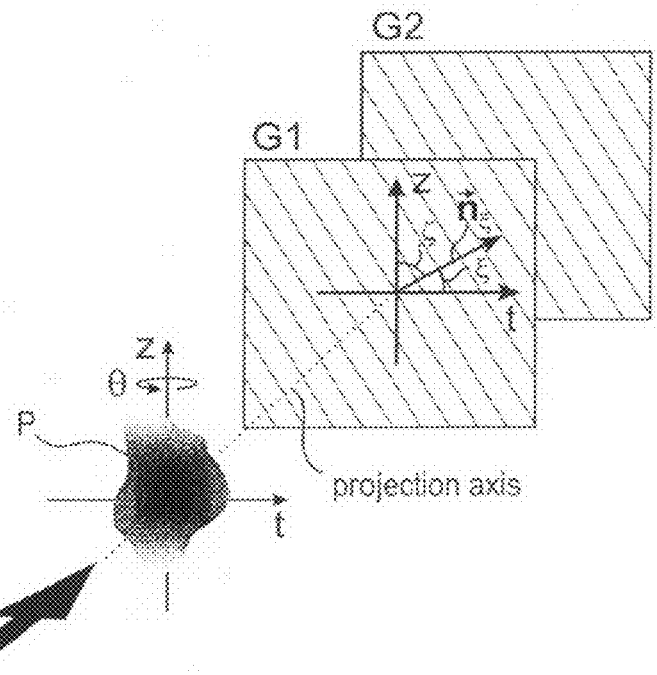
FIG. 1 shows a laboratory arrangement of a Talbot interferometer for measuring the differential phase contrast with a punctiform coherent X-ray source.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows an illustration of a measurement arrangement according to an embodiment of the invention, with a Talbot interferometer for the parallel beam case with a phase grid G1, an analysis grid G2 and a punctiform coherent radiation source emitting X-ray radiation y. With the exception of the orientation of the grid structures, such an arrangement is well known.

According to the definition, the normal vector $\vec{n}_\xi$ of the grid structure is perpendicular to the grid lines of the grids G1, G2 and describes the direction for which the directional derivative of the projections p is determined. This image is only a schematic illustration, particularly in respect of the scale, the shape of the grids, grid periods and scanning ratio, as well as the distances between the grids and the position of the examination object P. The angle θ describes the relative rotation of the examination object about the tomographic rotational axis z (=z-axis=system axis of the gantry of a CT system). The t-axis, which is situated in the plane of the grids or the projection, is illustrated orthogonally with respect to the z-axis. The relative rotation between the examination object P and the measurement arrangement can, as illustrated in this case, be implemented by a rotation of the examination object, and by a rotation of the measurement arrangement, about the examination object, as is conventional in the case of clinical phase-contrast CT systems.

Figure 2:
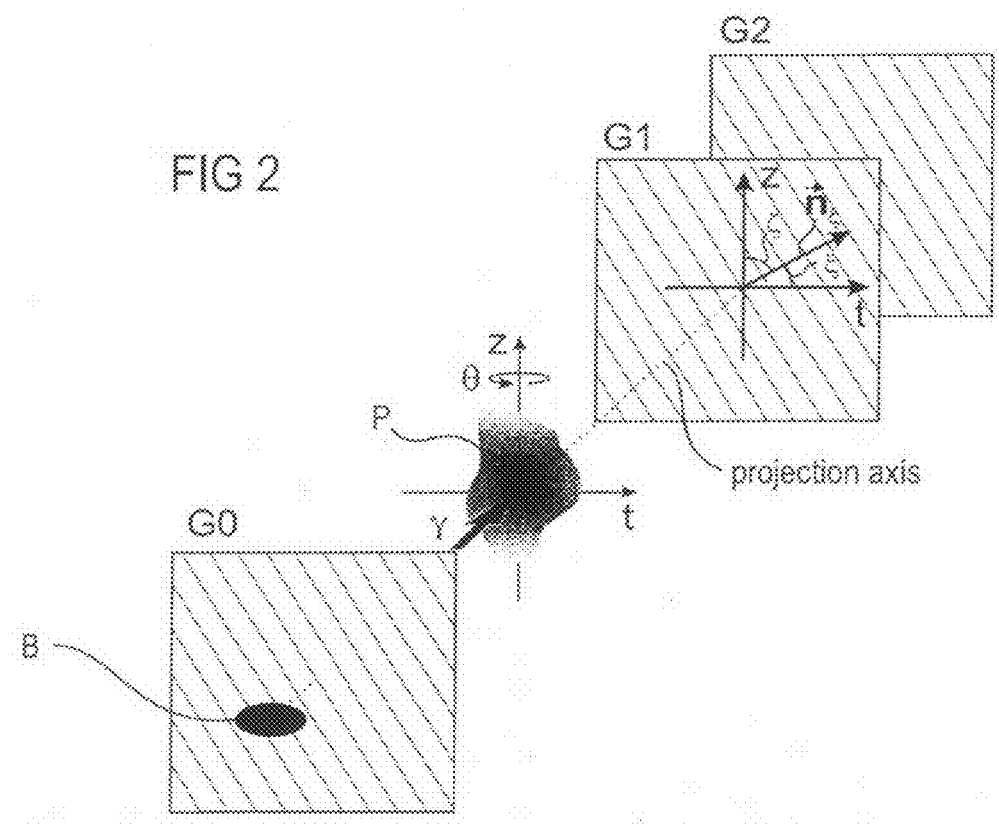
FIG. 2 shows a laboratory arrangement of a Talbot interferometer for measuring the differential phase contrast with an areal focal point and source grid.

A similar illustration of a measurement arrangement which does not exhibit the parallel beam case is shown in FIG. 2. Here, an incoherent source with a spatially expanded focal spot B is used as the radiation source, with a quasi-coherent X-ray radiation y being generated by the source grid G0 arranged in the beam path between the focal spot B and the examination object P.

In both cases illustrated above, the examination object P can be rotated about an angle of rotation of θ=180° and so the examination object P is—when viewed in the coordinate system of the examination object—respectively scanned with grids whose orientation has been mirrored.

Figure 3:
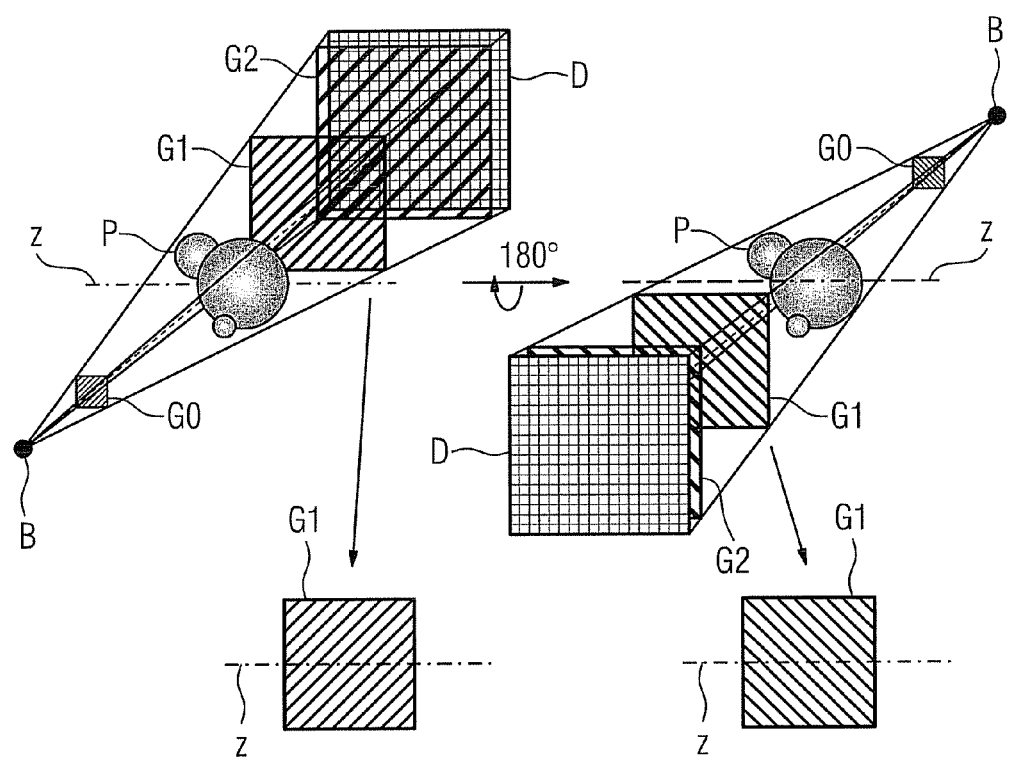
FIG. 3 shows an illustration of the measurement principle using a phase grid tilted by 45° with an emitter-detector system rotating about the examination object.

A similar situation is shown in FIG. 3. Here, an examination object P, comprising three spheres, is scanned by a measurement arrangement comprising a focal spot of the X-ray source B, three grids G0, G1 and G2 for the phase-contrast measurement and a detector D using two phase scans with phase grids oriented in a mirror-imaged fashion on the same projection axis, illustrated by dots, but with opposing projection directions. Herein, the examination object P appears on the detector in a mirrored fashion with phase grids G1 rotated by 90° relative to the system axis or rotational axis z.

Figure 4:
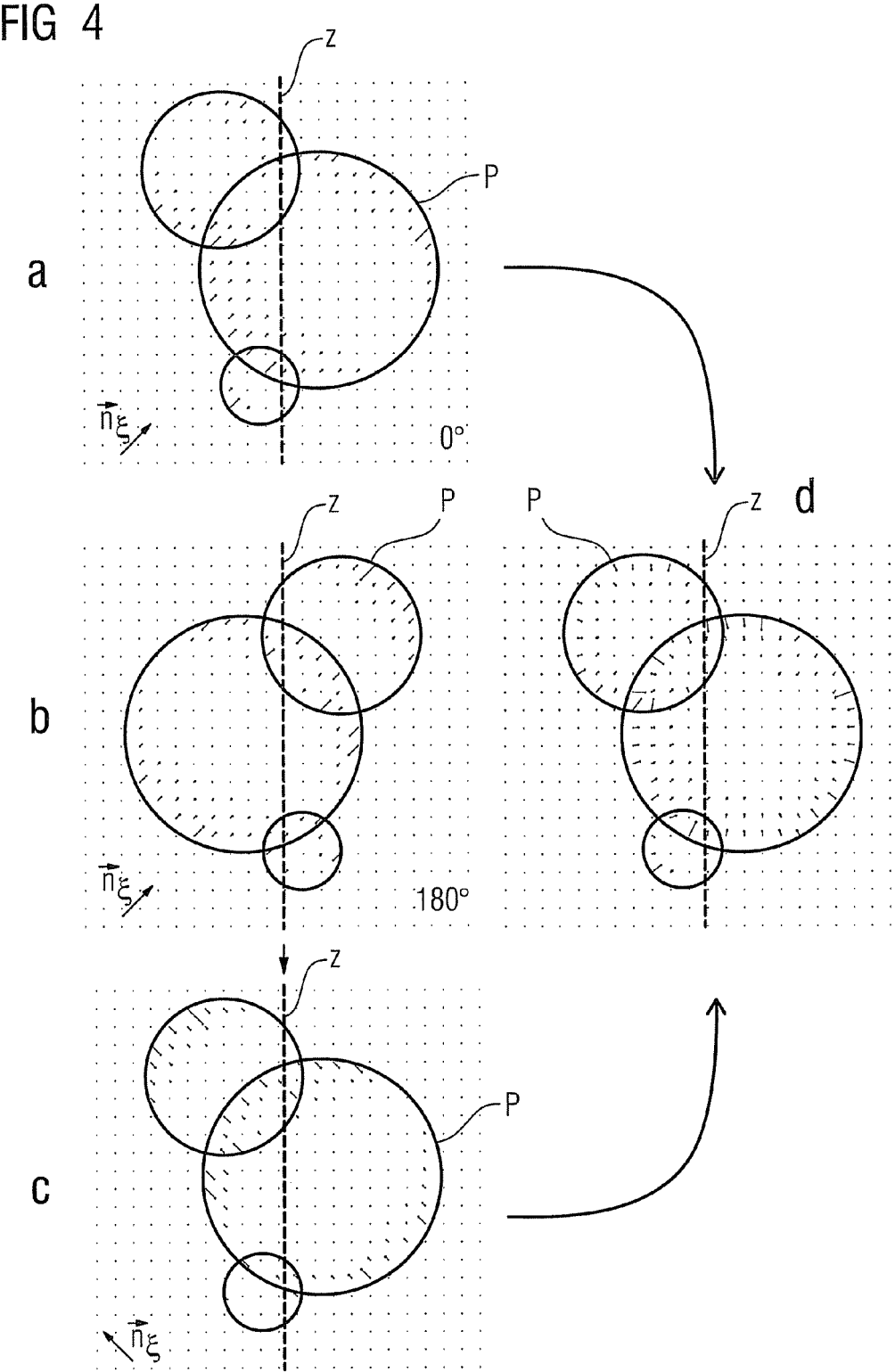
FIG. 4 shows an illustration of the measurement results in the case of three ideal spherical examination objects when using a phase grid tilted by 45°.

If the examination object P is measured using two phase scans by such an arrangement, this results in measurement results as are illustrated in FIG. 4.

A two-dimensional detector aligned parallel to the rotational axis was simulated in this FIG. 4 and so the rotational axis is projected into the center of the detector. Even though a two-dimensional detector could be oriented arbitrarily with respect to the grids and the rotational axis, this arrangement does seem to be advantageous. Thus, projection measured offset by 180° can be recorded with the same width on the same detector row. Since the data in this arrangement can be evaluated row-by-row, it goes without saying that a narrower or one-dimensional (row) detector can also be used.

Since the positions of the measurement points do not necessarily correspond to one another in the projections offset by 180°, the data has to be interpolated when combining the directional gradients. To this end, use can be made of standard methods such as "nearest neighbor" or "bi-linear" interpolation.

The measurement can be performed with interlaced sampling of the projection angles θ and so the projection pairs are not offset by precisely $\theta_2-\theta_1=180°$. This can attain a higher effective number of different projections and thus an improved resolution. The above-described interpolation should in this case also be extended to the projection angle dimension θ.

In the case of a fan beam or conical beam, the projections measured offset by $\theta_2-\theta_1=180°$ only correspond to the same projection integrals in the central beam through the rotational axis. However, the measurement values can be assigned to one another in the case of a fan beam using a fan beam resorting algorithm. In the case of the central conical beam, which likewise constitutes a fan beam, this is likewise possible. For the layers situated above and below the central plane, the resorting can be carried out in an approximate fashion.

In order to measure the directional derivatives, a so-called phase scan is performed using the interferometer. In the process, one of the grids is moved, continuously or incrementally, relative to the other grids over one or more grid periods. As a result of a suitable choice of the movement direction, it is also possible for a step-down to be obtained in the phase scan, as a result of which the requirement on the mechanical component for the grid movement in terms of positional accuracy is reduced. This step-down is possible because the grids of the interferometer have a one-dimensional structure and only the movement component parallel to the normal of the grid structure is relevant to the phase scan.

As a result, the two measurement results of partial figures a and b in FIG. 4 are obtained. It can easily be seen that the examination object P is illustrated in a mirrored fashion about the system axis or rotational axis z. The small vectors at the measurement points show the gradient of the phase shift at the respective measurement location perpendicular to the alignment of the grid lines of the utilized phase grid. By mirroring the measurement results from partial figure b, the illustration of partial figure c is obtained in which the orientation of the examination object P now corresponds to that of partial figure a, but the alignment of the phase grid and thus the measured gradient vectors now runs perpendicularly with respect to the partial figure a. Since the components of the gradient vectors are now available in two mutually different directions, the complete gradient vectors with magnitude and direction can be calculated from these measurement results. The result is shown in the partial figure d.

Figure 5:
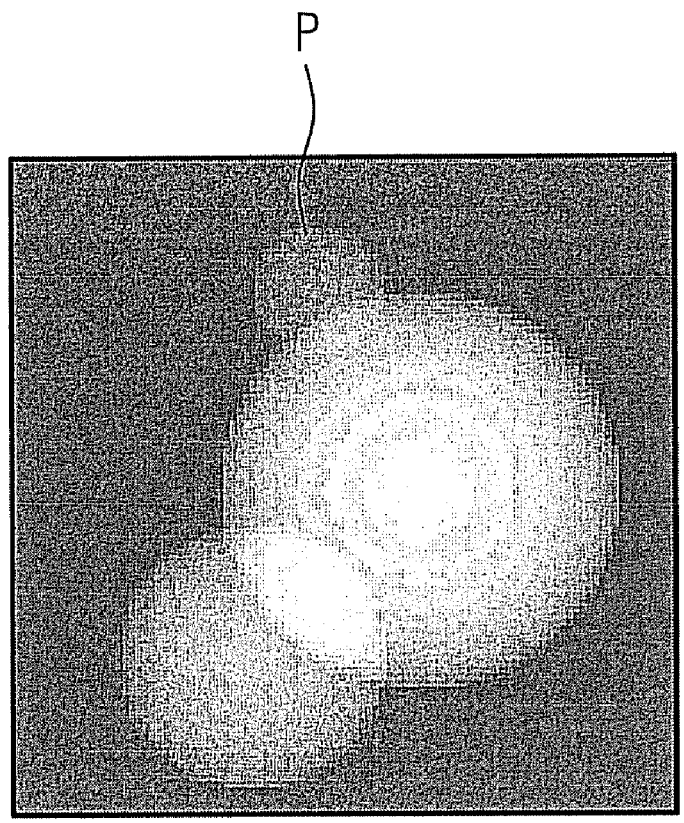
FIG. 5 shows a phase-contrast illustration of the three ideal spherical examination objects from FIGS. 3 and 4.

By integrating the complete gradient vectors assuming a known phase shift, the actual spatially occurring phase shift can now be calculated over the entire measurement field. The result of such a calculation is illustrated in FIG. 5, in which the grayscale values represent the present phase shift at each measurement point and the phase shift increases as the grayscale values becomes whiter. Thus, the illustration shows a projective reproduction or projection of the phase shift. If a multiplicity of such projections are measured over a projection angle of at least 180°, a tomographic illustration of an object can be calculated therefrom, wherein the pixel values of such an illustration reproduce the specific phase shift values in each volume element.

Figure 6:
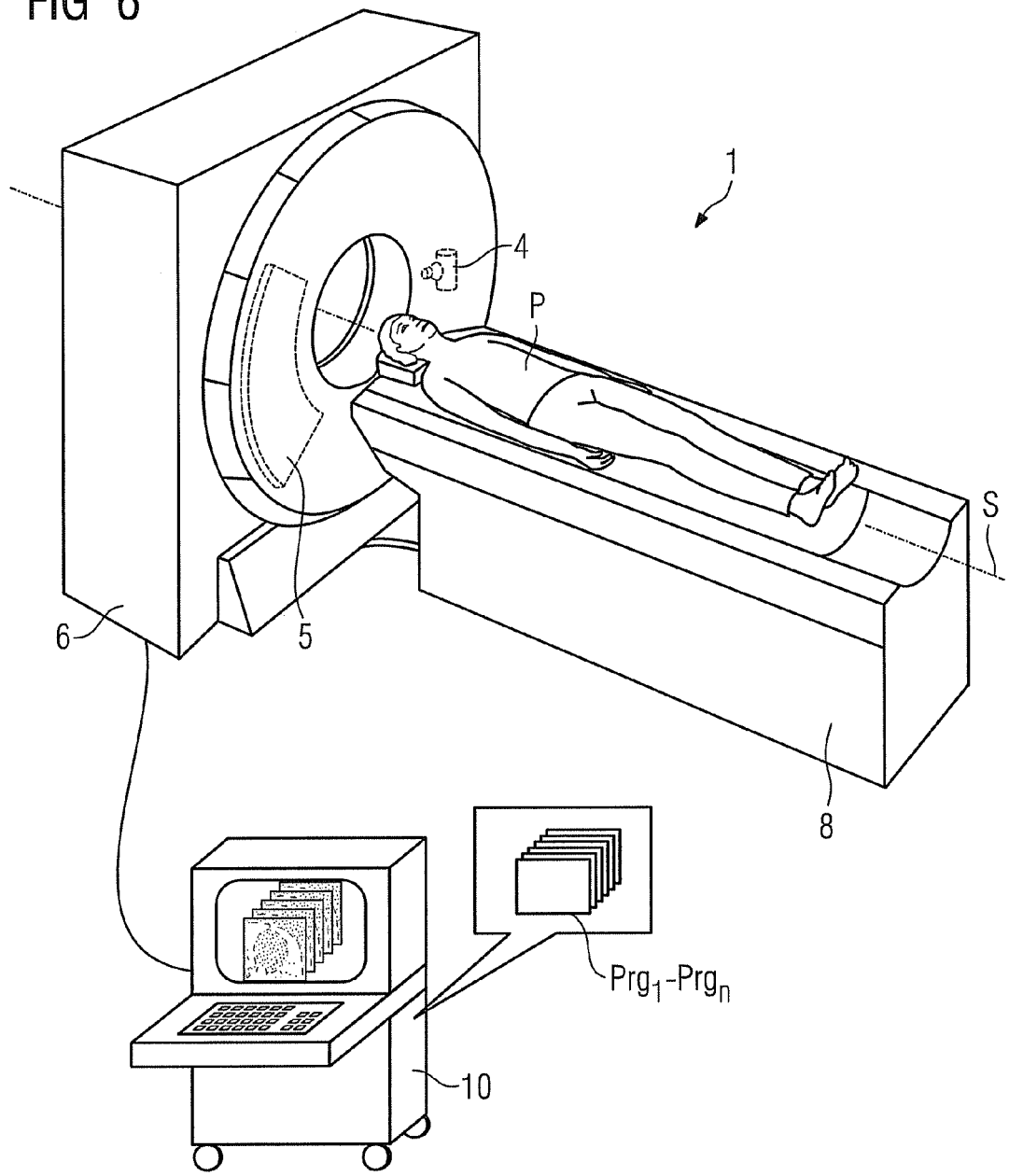
FIG. 6 shows a phase-contrast CT system with an emitter-detector system.

In practice, such a scan can be performed by a phase-contrast CT system 1 as shown in FIG. 6. In the housing 6, this system 1 has an emitter-detector arrangement with an X-ray tube 4 and a detector system 5 with X-ray optical grids G0, G1 and G2 similar to those of FIG. 3 located in the beam path (not illustrated in any more detail here). These X-ray optical grids G0, G1 and G2 are in the process tilted by an angle of incidence $\zeta=90°-\xi$ in relation to the projection of the system axis S onto the grid plane and so—as described above—the complete gradient vectors of the phase shift with magnitude and direction, and the phase shift in terms of the projection as well, can be determined by two oppositely aligned phase scans on the same projection axis. Using these measurement results, tomographic images of the patient P as the examination object can be determined. If the patient is, in the process, pushed through the measurement field of the CT system 1 with the aid of the displaceable couch table 8, it is possible for a slice image display to be reconstructed in a plurality of planes and a volume illustration of the phase shift values. The corresponding control of the CT system and the carrying out of the phase scans including the calculation of the projections and reconstruction of the image data can be performed by the control and computational unit 10 with the aid of the programs $Prg_1-Prg_n$ stored therein.

If two emitter-detector systems arranged offset at an angle and with differently tilted phase grids are used instead of a single emitter-detector system, the step of mirroring (from b to c in accordance with FIG. 4) can be dispensed with during the determination of the two spatial gradient components. FIG. 7 shows the results of two successively carried out measurements in the same projection direction with two measurement arrangements having differently tilted grids. Since the examination object P is in each case scanned in the same direction herein, the projection image d can be directly calculated from the results of the phase scans corresponding to partial figures a and b.

Figure 8B:
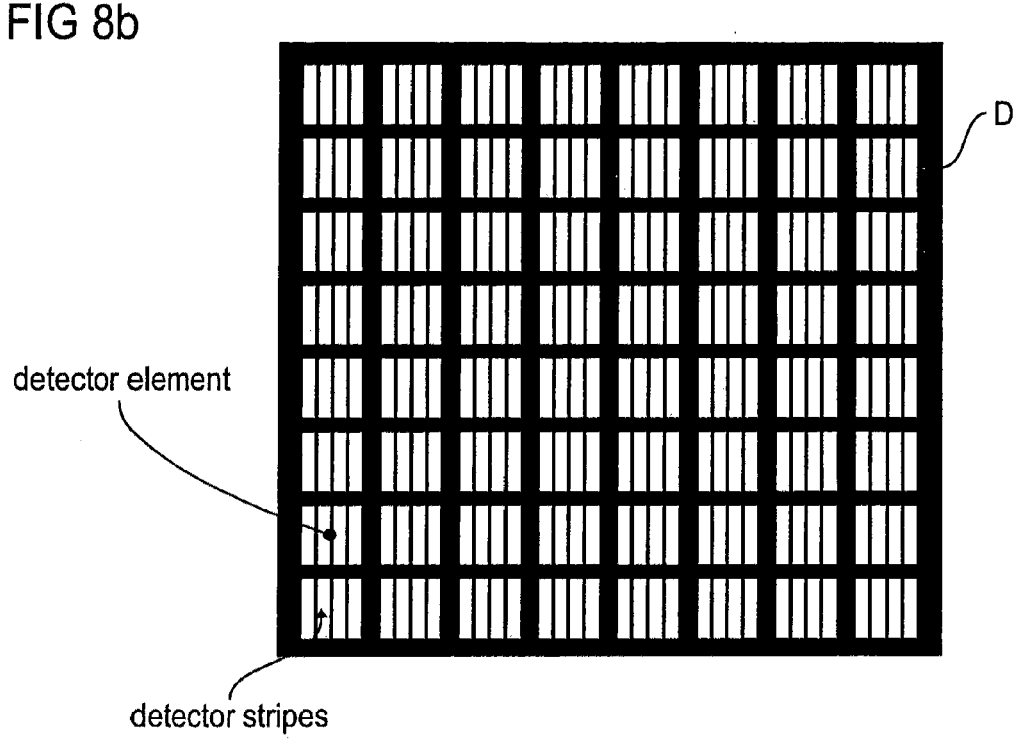
Figure 8C:
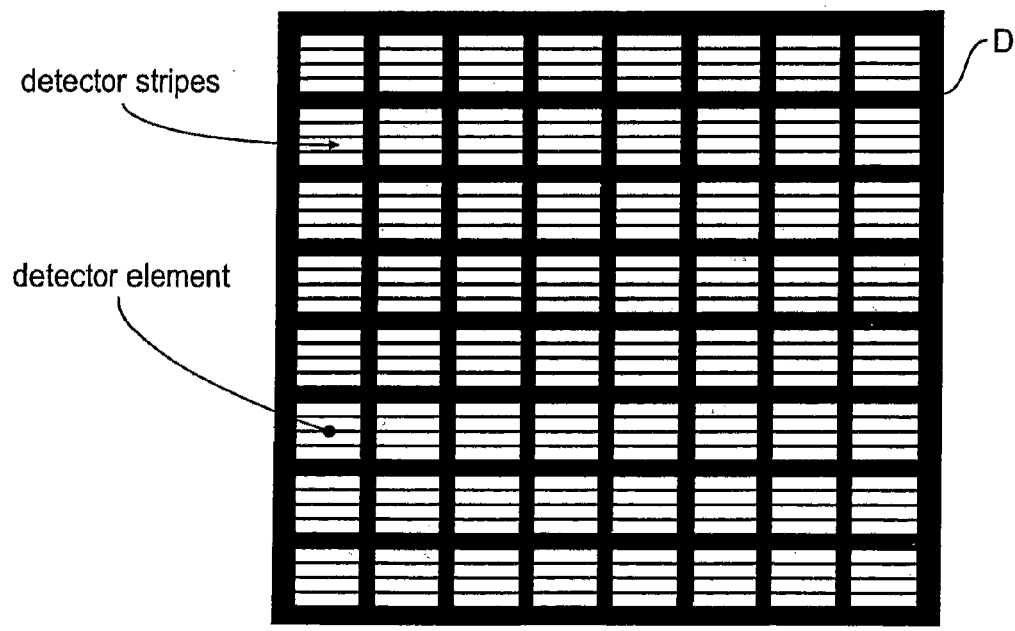

Schematic illustrations of two such measurements—but with angles of incidence of 0° and 90°—are shown in FIGS. 8a-8c. According to the invention, both measurement arrangements are in this case situated on a gantry and are arranged mutually offset at an angle of 90°, as is shown in the planar view of the gantry to the left and right, below the 3D illustrations.

Figure 9:
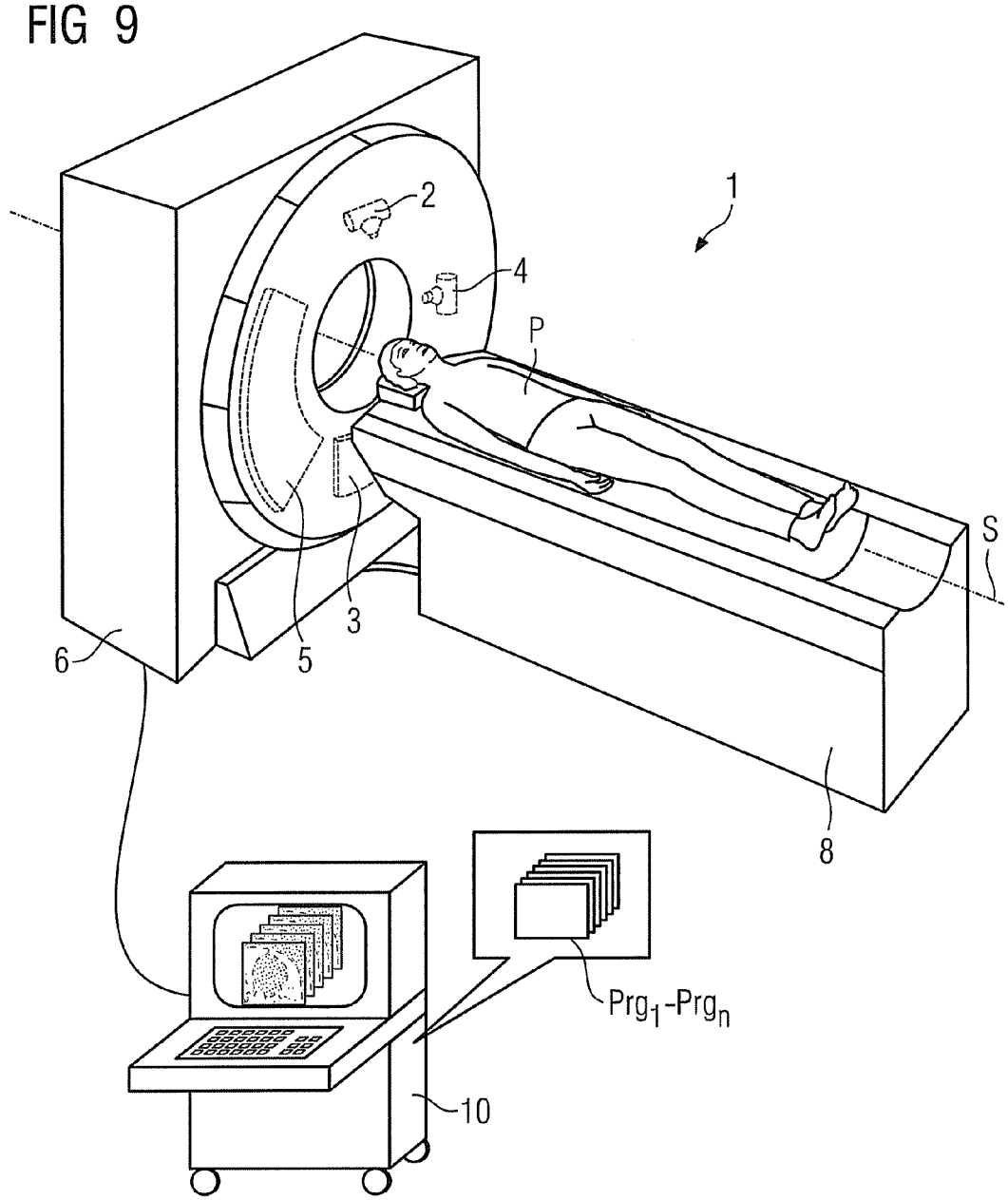
FIG. 9 shows a phase-contrast CT system with two emitter-detector systems with differently tilted phase grids.

FIG. 9 shows a corresponding phase-contrast CT system 1 with two emitter-detector systems with the X-ray tubes 2 and 4 and the detector systems 3 and 5 arranged offset at an angle of 90° in a housing 6 on a gantry. Each of the emitter-detector systems is respectively equipped with one phase grid for the phase-contrast measurement, which phase grids are arranged about the beam axis tilted by 90° in respect of one another at the same projection angle. As a result of this, phase scans in accordance with FIGS. 7 and 8 can be performed for each projection angle. Overall, these emitter-detector systems can respectively perform two phase scans at all projection angles over a range of 360° and thus phase-contrast data can also be determined and used for the reconstruction with a rotation of the gantry over the full angular range of 360°. The control of the CT system and the carrying out of the phase scans including the calculation of the projections and reconstruction of the image data can also in this case be performed by the control and computational unit 10 with the aid of the programs $Prg_1$–$Prg_n$ stored therein.

Thus, overall, this invention shows an arrangement and a method for projective and/or tomographic phase-contrast imaging using X-ray radiation, wherein one or more phase grids is/are arranged in the beam path such that during a rotation of the at least one X-ray source, the examination object is scanned with different spatial orientations of the grid lines relative to the examination object such that the complete refraction angle, and hence the complete phase shift gradient, can be determined for each X-ray beam from the two scans with differently oriented phase grids in order to be able to show the phase shift of an examination object in terms of projections or in a tomographic image.

It goes without saying that the abovementioned features of the invention can be used not only in the respectively specified combination but also in other combinations or on their own without departing from the scope of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An arrangement for at least one of projective and tomographic phase-contrast imaging using X-ray radiation, comprising:
   at least one coherent or quasi-coherent X-ray source to generate a beam path;
   a measurement field in which an examination object is positionable;

at least one one-dimensional phase grid with grid lines to generate an interference pattern, positioned in the beam path;

a readout arrangement for the generated interference pattern, arranged downstream of the at least one one-dimensional phase grid, to detect a change in a frequency pattern during a phase scan; and a control and evaluation unit to determine gradient vectors of phase shift values for the phase scan, the phase shift values being aligned perpendicularly with respect to the longitudinal direction of the grid lines of the at least one one-dimensional phase grid and situated in the plane of the at least one one-dimensional phase grid, wherein each of the at least one X-ray source associated with one of the at least one one-dimensional phase grid and the readout arrangement being configured, relative to the examination object, to rotate about a system axis, and the at least one one-dimensional phase grid is arranged in the beam path such that, during a rotation of the at least one X-ray source, the examination object is scanned with different spatial orientations of the grid lines relative to the examination object.

2. The arrangement as claimed in claim 1, further comprising a gantry, wherein two X-ray sources of the at least one coherent or quasi-coherent X-ray sources are provided on the gantry and the associated one-dimensional phase grid of each X-ray source have a different angle of incidence ($\zeta_1=90°-\xi_1$, $\zeta_2=90°-\xi_2$) between its grid lines and the system axis projected thereon in the beam direction.

3. The arrangement as claimed in claim 2, wherein the two angles of incidence ($\zeta_1=90°-\xi_1$, $\zeta_2=90°-\xi_2$) are perpendicular with respect to each other.

4. The arrangement as claimed in claim 3, wherein the two angles of incidence ($\zeta_1=90°-\xi_1$, $\zeta_2=90°-\xi_2$) are 0° and 90°.

5. The arrangement as claimed in claim 2, wherein the two angles of incidence ($\zeta_1=90°-\xi_1$, $\zeta_2=90°-\xi_2$) are set such that the error in the reconstruction is minimized.

6. The arrangement as claimed in claim 1, wherein the at least one one-dimensional phase grid is arranged in a beam path from the at least one X-ray source and the at least one one-dimensional phase grid has an angle of incidence ($\zeta=90°-\xi$) between its grid lines and the system axis projected thereon in the beam direction which does not equal an integer multiple of a right angle.

7. The arrangement as claimed in claim 6, wherein the angle of incidence ($\zeta=90°-\xi$) lies between 10° and 80°.

8. The arrangement as claimed in claim 7, wherein the angle of incidence ($\zeta=90°-\xi$) lies between 30° and 60°.

9. The arrangement as claimed in claim 8, wherein the angle of incidence is 45°.

10. The arrangement as claimed in claim 6, wherein the angle of incidence ($\zeta=90°-\xi$) is selected such that the error in the reconstruction is minimized.

11. The arrangement as claimed in claim 1, wherein the readout arrangement comprises an analysis grid and an at least single-row detector.

12. The arrangement as claimed in claim 1, wherein the readout arrangement comprises a detector which has a multiplicity of strip-shaped detection strips which can be read out individually aligned with the grid lines of the at least one one-dimensional phase grid for each of the multiplicity of strip-shaped detection strips.

13. The arrangement as claimed in claim 1, wherein the at least one X-ray source is configured as an almost punctiform source.

14. The arrangement as claimed in claim 1, further comprising:

a source grid for generating quasi-coherent radiation is arranged in the beam path between the at least one X-ray source and the at least one one-dimensional phase grid.

15. A method for generating at least one of projective and tomographic image data records with differential phase contrast using X-ray radiation, comprising:

scanning on a projection axis an examination object with at least one coherent or quasi-coherent X-ray source and at least one one-dimensional phase grid arranged in a beam path, wherein at least two phase scans with a respectively differently oriented phase grid of the at least one one-dimensional phase grids are performed for the projection axis;

determining gradient vectors of phase shift values for each of the at least two phase scans, the phase shift values being aligned perpendicularly with respect to the longitudinal direction of grid lines of the at least one one-dimensional phase grid and situated in the plane of the at least one one-dimensional phase grid; and calculating gradient vectors of the phase shift values, with magnitude and direction in the plane of the at least one one-dimensional phase grid, from the at least two phase scans of the projection axis.

16. The method as claimed in claim 15, wherein local phase shift values are calculated from the gradient vectors by integrating line integrals.

17. The method as claimed in claim 16, wherein the local phase shift values are determined for a plurality of projection angles over at least 180° and that computed tomography image data is reconstructed from this projection data.

18. The method as claimed in claim 15, wherein local phase shift values are determined for a plurality of projection angles over at least 180° and that computed tomography image data is reconstructed from projection data associated with the local phase shift values.

19. The method as claimed in claim 15, wherein there are, for the projection axis, two phase scans in opposing directions using the X-ray source, phase grid and readout arrangement, with the system respectively being rotated by 180° around a system axis.

20. A method for generating at least one of projective and tomographic image data records with differential phase contrast using X-ray radiation, comprising:

scanning, on a projection axis, an examination object with at least one coherent or quasi-coherent X-ray source and at least one one-dimensional phase grid arranged in a beam path, wherein at least two phase scans with a respectively differently oriented phase grid are performed for the projection axis;

determining gradient vectors of phase shift values for each of the at least two phase scans, the phase shift values being aligned perpendicularly with respect to the longitudinal direction of grid lines of the at least one one-dimensional phase grid and situated in the plane of the at least one one-dimensional phase grid; and reconstructing tomographic local phase shift values directly from the determined gradient vectors.

21. The method as claimed in claim 20, wherein the reconstruction is performed directly using the two gradient vectors measured perpendicularly with respect to the grid lines of the at least one one-dimensional phase grid.

22. The method as claimed in claim 20, wherein the gradient vectors with magnitude and direction are calculated before the reconstruction from the two gradient vectors measured perpendicularly with respect to the grid lines of the at least one phase grid and wherein the reconstruction is performed therewith.

23. The method as claimed in claim 20, wherein for the projection axis there are two phase scans in opposing directions using the X-ray source, the at least one one-dimensional phase grid and readout arrangement, with the system respectively being rotated by 180° around a system axis.

24. A method for generating at least one of projective and tomographic image data records with differential phase contrast using X-ray radiation, using an arrangement as claimed in claim 1, the method comprising:
- scanning on a projection axis an examination object with at least one coherent or quasi-coherent X-ray source and at least one one-dimensional phase grid arranged in a beam path, wherein at least two phase scans with a respectively differently oriented phase grid are performed for the projection axis;
- determining gradient vectors of phase shift values for each of the at least two phase scans, the phase shift values being aligned perpendicularly with respect to the longitudinal direction of grid lines of the at least one one-dimensional phase grid and situated in the plane of the at least one one-dimensional phase grid; and
- calculating gradient vectors of the phase shift values, with magnitude and direction in the plane of the at least one one-dimensional phase grid, from the at least two phase scans of the projection axis.

25. A method for generating at least one of projective and tomographic image data records with differential phase contrast using X-ray radiation, using an arrangement as claimed in claim 1, the method comprising:
- scanning, on a projection axis, an examination object with at least one coherent or quasi-coherent X-ray source and at least one one-dimensional phase grid arranged in a beam path, wherein at least two phase scans with a respectively differently oriented phase grid are performed for the projection axis;
- determining gradient vectors of phase shift values for each of the at least two phase scans, the phase shift values being aligned perpendicularly with respect to the longitudinal direction of grid lines of the at least one one-dimensional phase grid and situated in the plane of the at least one one-dimensional phase grid; and
- reconstructing tomographic local phase shift values directly from the determined gradient vectors.

26. A non-transitory computer readable medium including program segments for, when executed on a computer device, causing the computer device to implement the method of claim 15.

27. A non-transitory computer readable medium including program segments for, when executed on a computer device, causing the computer device to implement the method of claim 20.

* * * * *